US005641488A

United States Patent [19]
Wysocki

[11] Patent Number: 5,641,488
[45] Date of Patent: Jun. 24, 1997

[54] METHOD FOR PRODUCING AN ANTIBODY TO A CHOSEN ANTIGEN

[75] Inventor: Lawrence Wysocki, Denver, Colo.

[73] Assignee: National Jewish Center for Immunology and Respiratory Medicine, Denver, Colo.

[21] Appl. No.: 40,204

[22] Filed: Apr. 1, 1993

[51] Int. Cl.$^6$ .................. C07K 16/44; A61K 39/385
[52] U.S. Cl. .................. 424/184.1; 424/193.1; 530/388.1; 530/388.9; 530/389.1; 530/389.8
[58] Field of Search .................. 530/388.1, 388.9, 530/389.1, 389.8; 424/88, 184.1, 193.1

[56] References Cited

PUBLICATIONS

Ellenberger et al., "Recruiting Memory B Cells With Changed Antigenic Specificity", J. Immunol. 151(10): 5272–5281 (Nov. 15, 1993).

Liu et al., "Sequencing heavy–and light–chain variable genes of single B–hybridoma cells by total enzymatic amplification", Proc. Natl. Acad. Sci. 89: 7610–7614 (Aug. 1992).

Strong et al., "Three Dimensional Structure of Murine Anti–p–azophenylarsonate Fab 36–71. 1. X–ray Crystallography, Site–Directed mutagenesis, and Modeling of the Complex with Hapten", Biochem. 30(15): 3739–3748 (1990).

Parhami–Seren et al., "Clustered H Chain Somatic Mutations Shared by Anti–p–Azophenylarsonate Antibodies Confer Enhanced Affinity And Ablate The Cross Reactive Idiotype", J. Immunol. 245(7): 2340–2346 (Oct. 1990).

Wysocki et al., "Parallel Evolution of Antibody Variable Regions by Somatic Processes: Consecutive Shared Somatic Alterations in $V_H$ Genes Expressed by Independently Generated Hybridoma Apparently Acquired by Point Mutation and Selection Rather than by Gene Conversation", J. Exp. Med. 172: 315–323 (1990).

Fish et al., "Molecular Analysis of Original Antigenic Sin:," J. Exp. Med. 170:1191–1209 (Oct. 1989).

Wysocki et al., "Single Germline $V_H$ and $V_K$ Genes Encode Predominanting Anti–body Variable Regions Elicited in Strain A Mice By Immunization with p–Azopehnylarsonate", J. Exp. Med. 166: 1–11 (Jul. 1987).

Manser et al., "Evolution of Antibody Variable Region Structure During the Immune Response", Immunol. Rev. 96: 141–162 (1987).

Wysocki et al., "Somatic evolution of variable region structures during an immune response", Proc. Natl. Acad. Sci. USA 83: 1847–1851 (Mar. 1986).

Wysocki et al., "Combination Diversity Within Variable Regions Bearing The Predominant Anti–p–Azophenylarsonate Idiotype of Strain A Mice", J. Immunol. 134(4):2740–2747 (Apr. 1985).

Manser et al., "Isolation of hybridomas expressing a specific heavy chain variable region gene segment by using a screening technique that detects mRNA sequences in whole cell lysates", Immunol. 81: 2470–2474 (Apr. 1984).

Rothstein. "Affinity Analysis of Idiotype–Positive and Idiotype Negative Ars–Binding Hybridoma, Proteins & Ars–Immune Sera", Mol. Immunol. 20(2): 161–168 (1983).

Siekevitz, "The Genetic basis of antibody production; a single heavy chain variable region gene encodes all molecules bearing the dominant anti–arsonate idiotype in the strain A mouse", Eur. J. Immunol. 13: 123–132 (1983).

Woodland et al., "Idiotype–specific T Helper cells are required to induce idiotype positive B memory cells to secrete antibody", Eur. J. Immunol. 8: 600–606 (1978).

Vanden Berg et al., Immunology, 1980, 40:673.

Goding, Monoclonal Antibodies:Principles & Practice, 1986, pp. 61–62.

Wilhelm et al., Crit. Rev. Eucary Gene Express., 1992, 2(2)111–135.

*Primary Examiner*—Frank C. Eisenschenk
*Attorney, Agent, or Firm*—Sheridan Ross P.C.

[57] ABSTRACT

The invention relates to a method for producing antibodies of desired specificity. In particular, the method involves immunizing a subject animal with the chosen antigen following prior stimulation of the non-human animal's B cells. The prior stimulation may be accomplished, e.g., by immunization with a first antigen which is different from the second antigen. In a particularly preferred embodiment, the animal is a transgenic animal containing a human immunoglobulin gene, such as a transgenic mouse.

5 Claims, 2 Drawing Sheets

SEQUENCE LISTING ( 1 ) GENERAL INFORMATION:

( i i i ) NUMBER OF SEQUENCES: 16

( 2 ) INFORMATION FOR SEQ ID NO: 1:

( i ) SEQUENCE CHARACTERISTICS:
( A ) LENGTH: 363 base pairs
( B ) TYPE: nucleic acid
( C ) STRANDEDNESS: single
( D ) TOPOLOGY: linear ( x i ) SEQUENCE DESCRIPTION: SEQ ID NO: 1:

```
GAGGTTCAGC  TTCAGCAGTC  TGGAGCTGAG  CTGGTGAGGG  CTGGGTCCTC  AGTGAAGATG      60

TCCTGCAAGG  CTTCTGGATA  TACATTCACA  AGCTACGGTA  TAAACTGGGT  GAAACAGAGG     120

CCTGGACAGG  GCCTGGAATG  GATTGGATAT  ATTAATCCTG  GAAATGGTTA  TACTAAGTAC     180

AATGAGAAGT  TCAAGGGCAA  GACCACACTG  ACTGTAGACA  AATCCTCCAG  CACAGCCTAC     240

ATGCAGCTCA  GAAGCCTGAC  ATCTGAGGAC  TCTGCAGTCT  ATTTCTGTGC  AAGATCNNNN     300

TACTATGGTG  GTAGCTACNN  NTTTGACTAC  TGGGGCCAAG  GCACCACTCT  CACAGTCTCC     360

TCA                                                                       363
```

( 2 ) INFORMATION FOR SEQ ID NO: 2:

( i ) SEQUENCE CHARACTERISTICS:
( A ) LENGTH: 363 base pairs
( B ) TYPE: nucleic acid (C) STRANDEDNESS: single
(D) TOPOLOGY: linear (xi) SEQUENCE DESCRIPTION: SEQ ID NO: 2:

| | | | | | |
|---|---|---|---|---|---|
| GAGGTTCAGC | TTCAGCAGTC | TGGAGCTGAG | CTGGTGAGGG | CTGGGTCCTC | AGTGAAGATG | 60 |
| TCCTGCAAGG | CTTCTGGATA | TACATTCACA | AGCTACGGTA | TAAGCTGGGT | GAAACAGAGG | 120 |
| CCTGGACAGG | GCCTCGAATG | GATTGGATAT | GTTAATCCTG | GAAATGGTTA | TACTAACTAC | 180 |
| AATGAGAAGT | TCAAGGGCAA | GACCCCACTG | ACTGTAGACA | AATCCTCCAG | CACAGTCTAC | 240 |
| ATGCAGCTCA | GAAGCCTGAC | ATCTGAGGAC | TCTGCAGTCT | ATTTCTGTGC | AAGATCCCAT | 300 |
| TACTATGGTG | GTAGCTACTC | CTTTCACTAC | TGGGGCCAAG | GCACCACTCT | CACAGTCTCC | 360 |
| TCA | | | | | | 363 |

(2) INFORMATION FOR SEQ ID NO: 3:

(i) SEQUENCE CHARACTERISTICS:
(A) LENGTH: 363 base pairs
(B) TYPE: nucleic acid
(C) STRANDEDNESS: single
(D) TOPOLOGY: linear (xi) SEQUENCE DESCRIPTION: SEQ ID NO: 3:

| | | | | | |
|---|---|---|---|---|---|
| GAGGTTCAGC | TTCAGCAGTC | TGGAGGTGAG | CTGGTGAGGG | CTGGGTCCTC | AGTGAAGATG | 60 |
| TCCTGCAAGG | CTTCTGGATA | TACATTCACA | AACTACGGTA | TAAGCTGGGT | GAAACAGAGG | 120 |
| CCTGGACAGG | GCCTGGAATG | GATTGGATAT | ATTAATCCTG | GAAATGATTA | TATAAACTAC | 180 |
| AATGAGAAGT | TCAAGGGCAA | GACCACACTG | ACTGTAGACA | AATCCTCCAG | CACAGCCTAC | 240 |
| ATGCAGCTCA | GAAGCCTGAC | ATCTGAGGAC | TCTGCAGTCT | ATTTCTGTGC | AAGATCCCAT | 300 |
| TACCATGGTG | GTAGCTACTG | CTTTGACTAC | TGGGGCCAAG | GCACCACTCT | CACAGTCTCC | 360 |
| TCA | | | | | | 363 |

(2) INFORMATION FOR SEQ ID NO: 4:

(i) SEQUENCE CHARACTERISTICS:
(A) LENGTH: 363 base pairs
(B) TYPE: nucleic acid
(C) STRANDEDNESS: single
(D) TOPOLOGY: linear (xi) SEQUENCE DESCRIPTION: SEQ ID NO: 4:

| | | | | | |
|---|---|---|---|---|---|
| GAGGTTCAGC | TTCAGCAGTC | TGGAGGTGAG | CTGGTGAGGG | CTGGGTCCTC | AGTGAAGATG | 60 |
| TCCTGCAAGG | CTTCTGGATA | TACATTCACA | AGCTACGGTA | TAAGCTGGGT | GAAACAGAGG | 120 |
| CCTGGACAGG | GCCTGGAATG | GATTGGATAT | ATTAATCCTG | GAAATGATTA | TATAAACTAC | 180 |
| AATGAGAAGT | TCAAGGGCAA | GACCACACTG | ACTGTAGACA | AATCCTCCAG | CACAGCCTAC | 240 |
| ATGCAGCTCA | GAAGCCTGAC | ATCTGAGGAC | TCTGCAGTCT | ATTTCTGTGC | AAGATCCCAT | 300 |
| TACCATGGTG | GTAGCTACTG | CTTTGACTAC | TGGGGCCAAG | GCACCACTCT | CACAGTCTCC | 360 |
| TCA | | | | | | 363 |

(2) INFORMATION FOR SEQ ID NO: 5:

(i) SEQUENCE CHARACTERISTICS:
(A) LENGTH: 366 base pairs
(B) TYPE: nucleic acid
(C) STRANDEDNESS: single
(D) TOPOLOGY: linear (xi) SEQUENCE DESCRIPTION: SEQ ID NO: 5:

```
GAGGTTCAGC TTCAGCAGTC TGGAGCTGAG CTGGTGAGGG CTGGGTCCTC AGTGAAGATG      60

TCCTGCAAGG CTTCTGGATT TACATTCACA AGCTACGGTA TAAGCTGGGT GAAACAGAGG     120

CCTGGACAGG GCCTGGAATG GATTGGATAT ATTAATCCTG GAAATGTTTA TACTAACTAC     180

AATGAGAAGT TCAAGGGCAA GACCACACTG ACTGTAGACA AATCCTCCAG CACAGCCTAC     240

ATGCAGCTCA GAAGCCTGAC ATCTGAGGAC TCTGCAGTCT ATTTCTGTGC AAGATCGACC     300

TATTATAGCG GAGGGGGGTA CTACTTTGAC TACTGGGGCC AAGGCACCAC TCTCACAGTC     360

TCCTCA                                                                366
```

( 2 ) INFORMATION FOR SEQ ID NO: 6:

( i ) SEQUENCE CHARACTERISTICS:
        ( A ) LENGTH: 366 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 6:

```
GAGGTTCAGC TTCAGCAGTC TGGAGCTGAG CTGGTGAGGG CTGGGTCCTC AGTGAAGATG      60

TCCTGCAAGG CTTCTGGATA TACATTCACA GGCTACGGTA TAAGCTGGGT GAAACAGAGG     120

CCTGGACAGG GCCTGGAATG GATTGGATAT ATTAATCCTG GAAATGATTA TACTAATTAC     180

AATGAGAAGT TCAAGGGCAA GACCACACTG ACTGTAGACA AATCTTCCAG CACAGCCTAC     240

ATGCAGCTCA GAAGCCTGAC ATCTGAGGAC TCTGCAGTCT ATTTCTGTGC AAGATCCTTT     300

TATTACTATG GTGGTACCTA CGTCTTTGAC TACTGGGGCC AAGGCACCAC TCTCACAGTC     360

TCCTCA                                                                366
```

( 2 ) INFORMATION FOR SEQ ID NO: 7:

( i ) SEQUENCE CHARACTERISTICS:
        ( A ) LENGTH: 366 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 7:

```
GAGGTTCAGC TTCAGCAGTC TGGAGCTGAG CTGGTGAGGG CTGGGTCCTC AGTGAAGATG      60

TCCTGCAAGG CTTCTGGATA TACATTCACA GGCTACGGTA TAAGCTGGGT GAAACAGAGG     120

CCTGGACAGG GCCTGGAATG GATTGGATAT ATTAATCCTG GAAATGGTTA TACTAAGTAC     180

AATGAGAAAT TCAAGGGCAA GACCACACTG ACTGTAGACA AATCCTCCAG CACAGCCTAC     240

ATGCAGCTCA GAAGCCTGAC ATCTGAGGAC TCTGCAGTCT ATTTCTGTGC AAGATCTTCT     300

TTTTACTTTG GTGGTAGCTA CAGCTTTGAC TACTGGGGCC AAGGCACCAC TCTCACAGTC     360

TCCTCA                                                                366
```

( 2 ) INFORMATION FOR SEQ ID NO: 8:

( i ) SEQUENCE CHARACTERISTICS:
        ( A ) LENGTH: 363 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 8:

```
GAGCTTCAGC TTCAGCAGTC TGGAGCTGAG CTGGTGAGGG CTGGGTCCTC AGTGAAGATG      60

TCCTGCAAGG CTTCTGGATA TACATTCACA AGCTACGGTA TAACCTCCCT GACACAGAGG     120

CCTGGACAGG GCCTGGAATG GATTCCATAT ATTAATCCTG GAAATGGTTA TATTACGTAC     180
```

| | | | | | |
|---|---|---|---|---|---|
| AATGAGAAGT | TCAAGGGCAA | GACCACACTG | ACTGTAGACA | AATCCTCCAG | CACAGCCTAC | 240
| ATGCAGCTCA | GAAGCCTGAC | ATCTGAGGAC | TCTGCAGTCT | ATTTCTGTGC | AAGATCTTAC | 300
| TATGGTGGTA | GTTATTGGTA | CTTCCATGTC | TGGGGCACAG | GGACCACGGT | CACACTCTCC | 360
| TCA | | | | | | 363

(2) INFORMATION FOR SEQ ID NO: 9:

(i) SEQUENCE CHARACTERISTICS:
        (A) LENGTH: 324 base pairs
        (B) TYPE: nucleic acid
        (C) STRANDEDNESS: single
        (D) TOPOLOGY: linear (xi) SEQUENCE DESCRIPTION: SEQ ID NO: 9:

| | | | | | |
|---|---|---|---|---|---|
| GATATCCAGA | TGACACAGAC | TACATCCTCC | CTGTCTGCCT | CTCTGGGAGA | CAGAGTCACC | 60
| ATCAGTTGCA | GGGCAAGTCA | GGACATTAGC | AATTATTTAA | ACTGGTATCA | GCAGAAACCA | 120
| GATGGAACTG | TTAAACTCCT | GATCTACTAC | ACATCAAGAT | TACACTCAGG | AGTCCCATCA | 180
| AGGTTCAGTG | GCAGTGGGTC | TGGAACAGAT | TATTCTCTCA | CCATTAGCAA | CCTGGAGCAA | 240
| GAAGATATTG | CCACTTACTT | TTGCCAACAG | GGTAATACGC | TTCCTCGGAC | GTTCGGTGGA | 300
| GGCACCAAGC | TGGAAATCAA | ACGT | | | | 324

(2) INFORMATION FOR SEQ ID NO: 10:

(i) SEQUENCE CHARACTERISTICS:
        (A) LENGTH: 324 base pairs
        (B) TYPE: nucleic acid
        (C) STRANDEDNESS: single
        (D) TOPOLOGY: linear (xi) SEQUENCE DESCRIPTION: SEQ ID NO: 10:

| | | | | | |
|---|---|---|---|---|---|
| GATATCCAGA | TGACACAGAC | TACATCCTCC | CTGTCTGCCT | CTCTGGGAGA | CAGAGTCACC | 60
| ATCAGTTGCA | GGGCAAGTCA | GGACATTAGC | AATTATTTAA | ACTGGTATCA | GCAGAAACCA | 120
| GATGGAACTG | TTAAACTCCT | GATCTACTAC | ACATCAAGAT | TACACTCAGG | AGTCCCATCA | 180
| AGGTTCAGTG | GCAGTGGGTC | TGGAACAGAT | TATTCTCTCA | CCATTAGCAA | CCTGGAGCAA | 240
| GAAGATATTG | CCACTTACTT | TTGCCAACAA | GGTAATACGC | TTCCTCGGAC | GTTCGGTGGA | 300
| GGCACCAAGG | TGGAAATCAA | ACGT | | | | 324

(2) INFORMATION FOR SEQ ID NO: 11:

(i) SEQUENCE CHARACTERISTICS:
        (A) LENGTH: 324 base pairs
        (B) TYPE: nucleic acid
        (C) STRANDEDNESS: single
        (D) TOPOLOGY: linear (xi) SEQUENCE DESCRIPTION: SEQ ID NO: 11:

| | | | | | |
|---|---|---|---|---|---|
| GATATCCAGA | TGACACAGAC | TACATCCTCC | CTGTCTGCCT | CTCTGGGAGA | CAGAGTCACC | 60
| ATCAGTTGCA | GGGCAAGTCA | GGACATTAAC | AATTATTTAA | ACTGGTATCA | GCAGAAACCA | 120
| GATGGAACTG | TTAAACTCCT | GATCTACTAC | ACATCAAGAT | TACACTCAGG | AGTCCCATCA | 180
| AGGTTCAGTG | GCAGTGGGTC | TGGAACAGAT | TATTCTCTCA | CCATTAGCAA | CCTTGAACAA | 240
| GAAGATATTG | CCACTTACTT | TTGCCAACAG | GGTAATACGC | TTCCTCGGAC | GTTCGGTGGA | 300
| GGCACCAAGC | TGGAAATCAA | ACGT | | | | 324

(2) INFORMATION FOR SEQ ID NO: 12:

( i ) SEQUENCE CHARACTERISTICS:
( A ) LENGTH: 324 base pairs
( B ) TYPE: nucleic acid
( C ) STRANDEDNESS: single
( D ) TOPOLOGY: linear ( x i ) SEQUENCE DESCRIPTION: SEQ ID NO: 12:

| | | | | | |
|---|---|---|---|---|---|
| GATATCCAGA | TGACACAGAC | TACATCCTCC | CTGTCTGCCT | CTCTGGGAGA | CAGAGTCACC | 60
| ATCAGTTGCA | GGGCAAGTCA | GGACATTAAC | AATTATTTAA | ACTGGTATCA | GCAGAAACCA | 120
| GATGGAACTG | TTAAACTCCT | GATCTACTAC | ACATCAAGAT | TACACTCAGG | AGTCCCATCA | 180
| AGGTTCAGTG | GCAGTGGGTC | TGGAACAGAT | TATTCTCTCA | CCATTAGCAA | CCTTGAACAA | 240
| GAAGATATTG | CCACTTACTT | TTGCCAACAG | GGTAATACGC | TTCCTCGGAC | GTTCGGTGGA | 300
| GGCACCAAGC | TGGAAATCAA | ACGT | | | | 324

( 2 ) INFORMATION FOR SEQ ID NO: 13:

( i ) SEQUENCE CHARACTERISTICS:
( A ) LENGTH: 324 base pairs
( B ) TYPE: nucleic acid
( C ) STRANDEDNESS: single
( D ) TOPOLOGY: linear ( x i ) SEQUENCE DESCRIPTION: SEQ ID NO: 13:

| | | | | | |
|---|---|---|---|---|---|
| GATATCCAGA | TGACACAGAC | TACATCCTCC | CTGTCTGCCT | CTCTGGGAGA | CAGAGTCACC | 60
| ATCAGTTGCA | GGGCAAGTCA | GGACATTAGC | AATTATTTAA | ACTGGTATCA | GCAGAAACCA | 120
| GATGGAACTG | TTAAACTCCT | GATCTACTAC | ACATCAAGAT | TACACTCAGG | AGTCCCATCA | 180
| AGGTTCAGTG | GCAGTGGGTC | TGGAACAGAT | TATTCTCTCA | CCATCAGCAA | CCTGGAGCAA | 240
| GAAGATATTG | CCACTTACTT | TTGCCAACAG | GGTAATACGC | TTCCTCGGAC | GTTCGGTGGA | 300
| GGCACCAAGC | TGGAAATCAA | ACGT | | | | 324

( 2 ) INFORMATION FOR SEQ ID NO: 14:

( i ) SEQUENCE CHARACTERISTICS:
( A ) LENGTH: 324 base pairs
( B ) TYPE: nucleic acid
( C ) STRANDEDNESS: single
( D ) TOPOLOGY: linear ( x i ) SEQUENCE DESCRIPTION: SEQ ID NO: 14:

| | | | | | |
|---|---|---|---|---|---|
| GATATCCAGA | TGACACAGAC | TACATCCTCC | CTGTCTGCCT | CTCTGGGAGA | CAGAGTCACC | 60
| ATCAGTTGCA | GGGCAAGTCA | GGACATTTAC | AATTATTTAA | ACTGGTATCA | GCAGAAACCA | 120
| GATGGAACTG | TTAAACTCCT | GATCTACTAC | ACATCAAGAT | TACACTCAGG | AGTCCCATCA | 180
| AGGTTCAGTG | GCAGTGGGTC | TGGAACAGAT | TATTCTCTCA | CCATTAGCAA | CCTGGAGCAA | 240
| GAAGATATTG | CCACTTACTT | TTGCCAACAG | GGTAATACGC | TTCCTCGGAC | GTTCGGTGGA | 300
| GGCACCAAGC | TGGAAATCAA | ACGT | | | | 324

( 2 ) INFORMATION FOR SEQ ID NO: 15:

( i ) SEQUENCE CHARACTERISTICS:
( A ) LENGTH: 324 base pairs
( B ) TYPE: nucleic acid
( C ) STRANDEDNESS: single
( D ) TOPOLOGY: linear ( x i ) SEQUENCE DESCRIPTION: SEQ ID NO: 15:

| | | | | | |
|---|---|---|---|---|---|
| GATATCCAGA | TGACACAGAC | TACATCCTCC | CTGTCTGCCT | CTCTGGGAGA | CAGAGTCACC | 60

-continued

| | | | | | | |
|---|---|---|---|---|---|---|
| ATCAGTTGCA | GGGCAAGTCA | GGACATTAGC | AATTATTTAA | ACTGGTATCA | GCAGAAACCA | 120 |
| GATGGATCTG | TTAAACTCCT | GATCTACTAC | ACATCAAGAT | TACACTCAGG | AGTCCCATCA | 180 |
| AGGTTCAGTG | GCAGTGGGTC | TGGAACAGAT | TATTCTCTCA | CCATTAGCAA | CCTGGAGCAA | 240 |
| GAAGATATTG | CCACTTACTT | TTGCCAACAG | GGTAATACGC | TTCCTCGGAC | GTTCGGTGGA | 300 |
| GGCACCAAGC | TGGAAATCAA | ACGT | | | | 324 |

( 2 ) INFORMATION FOR SEQ ID NO: 16:

( i ) SEQUENCE CHARACTERISTICS:
        ( A ) LENGTH: 324 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 16:

| | | | | | | |
|---|---|---|---|---|---|---|
| GATATCCAGA | TGACACAGAC | TACATCCTCC | CTGTCTGCCT | CTCTGGGAGA | CAGAGTCACC | 60 |
| ATCAGTTGCA | GGGCAAGTCA | GGACATTAGC | AATTATTTAA | ACTGGTATCA | GCAGAAACCA | 120 |
| GATGGAAGTG | TTAAACTCCT | GATCTACTAC | ACATCAAGAT | TACACTCAGG | AGTCCCGTCA | 180 |
| AGGTTCAGTG | GCAGTGGGTC | TGGAACAGAT | TATTCTCTCA | CCATTAGCAA | CCTGGAGCAA | 240 |
| GAAGATATTG | CCACTTACTT | TTGCCAACAG | GGTAATACAC | TTCCTCGGAC | GTTCGGTGGA | 300 |
| GGCACCAAGC | TGGAAATCAA | ACGT | | | | 324 |

METHOD FOR PRODUCING AN ANTIBODY TO A CHOSEN ANTIGEN

FIELD OF THE INVENTION

This invention relates to immunology. More particularly, it relates to an improved method for making antibodies.

BACKGROUND AND PRIOR ART

The process by which antibodies are formed is a complex one, many of the particulars of which are, however, understood. In brief, an involved set of reactions and responses are set in motion whenever a foreign material, such as an antigen, is introduced to an animal with a functioning immune system. Mature B cells are triggered to produce antibodies via their interaction with antigen and helper T cells. These antibody molecules consist of a light chain and a heavy chain, and are coded for by genes present in the mammalian genome. Every light chain is coded for by three distinct gene segments—the $V_L$, $J_L$ and $C_L$ segments, while heavy chains are coded for by four segments, i.e., $V_H$, $D_H$, $J_H$ and $C_H$.

In light chains, the variable region is coded for by the "$V_L$" and "$J_L$" segments, whereas the variable region of heavy chains is coded for by "$V_H$", "$D_H$" and "$J_H$" segments. A number of different genes exist for each segment. Shuffling and rearrangement can lead to an estimated $10^6$–$10^7$ antibodies, coded for by different combinations of variable gene segments. In addition, at all three points at which the variable gene segments are joined, i.e., the "$V_H$-D", "D-$J_H$" and "$V_L$-$J_L$" junctures, substantial sequence variability is possible for any given pair of assembling segments. This junctional variability, together with the combinational diversity, can lead to an estimated $10^{12}$ different antibodies. A composite variable region, formed by pairing of the heavy and light chain variable regions, contains the antibody's binding site. This binding site is of major interest in connection with the subject invention.

When an antibody response to a T cell dependent antigen is mounted, those B cells with antibodies capable of engaging the antigen proliferate to form large clones. In addition, members of the B cell clone diversify their variable genes by a hypermutation mechanism. This diversification of the B cell clone is of central important to the invention.

The somatic mutation process is well recognized in the art, but is poorly understood. See, e.g., Crews et al., Cell 25: 56 (1981); Gearhart et al., Nature 291: 29 (1981); Bothwell et al., Cell 24: 625 (1981); Siekevitz et al., Eur. J. Immunol. 13: 123 (1983); Clarke et al., J. Exp. Med. 161: 687 (1985); Selsing et al., Cell 25: 47 (1981).

The time period during which mutational diversification occurs is not known, although it is known that somatic mutations are acquired at some stage of the primary immune response, and possibly during secondary and later response (Griffith et al., J. Immunol. 312: 271 (1984); Wysocki et al., Proc. Natl. Acad. Sci. USA 83: 1847 (1986); Levy et al., J. Exp. Med. 169: 2007 (1989)). The mutation process introduces, e.g., point nucleotide substitutions in the assembled antibody genes expressed by clones of immune participating B lymphocytes. Often these nucleotide substitutions result in amino acid replacements in the encoded antibody variable region. In this way, the antibodies expressed by different members of a mutationally active B cell clone may differ in variable region sequence and potentially in binding site structure and function as well. Changes in the antibody binding site that are the direct consequences of the somatic mutation process are of central importance in connection with the subject invention.

Somatic mutations are almost always found in the variable genes of memory B cells when these are sampled by hybridoma production. It has also been observed that recruitment into the memory B cell compartment of the immune repertoire is strongly correlated with acquisition of specific somatic mutations and combinations thereof which confer upon antibody product increased affinity for immunizing antigen. (See Moller ed., "Role of somatic mutation in the generation of lymphocyte diversity" in Immunol. Rev. 96: 162 (1987)). These observations suggest that only a slender fraction of a mutationally diversified clone of B cells is usually recruited into the memory compartment. The unobserved majority of a diversified population must presumably include members with antibodies whose affinity for stimulatory antigen has been reduced or abolished. (See Manser et al., J. Exp. Med. 166: 1456 (1987)). Some fraction of this majority, however, presumably retains the ability to produce antibodies. It has now been found that these mutant B cells can be stimulated to proliferate into "subclones" which are specific to a chosen antigen which is distinguishable from the antigen used in the first immunization. These subclones result, surprisingly, via immunizing a subject animal with the antigen of choice following stimulation of the animal via, e.g., immunization with a first immunogen. In effect, one can recruit "mutant" B cells which bind to and are stimulated by an antigen of interest but are derived originally from precursor B cells which were incapable of being stimulated by the antigen of interest. The examples which follow set forth how this is accomplished.

DETAILED DESCRIPTION OF PREFERRED EMBODIMENTS

Example 1

Figure 1A:
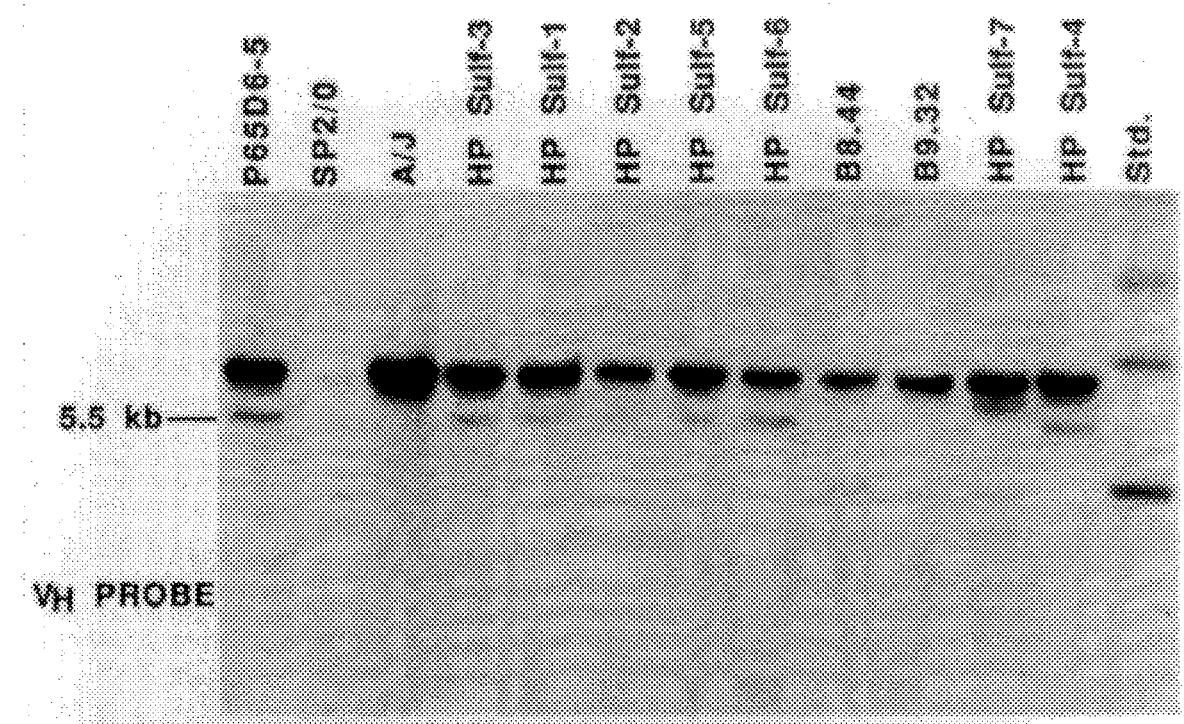
FIG. 1A presents Southern blotting analyses of $V_H$ and $V_K$ gene rearrangements in the DNA of Sulf specific hybridomas. The figure shows results from EcoRI digested DNA, hybridized with a $V_H Id^{CR}$ probe, using high stringency conditions.
Figure 1B:
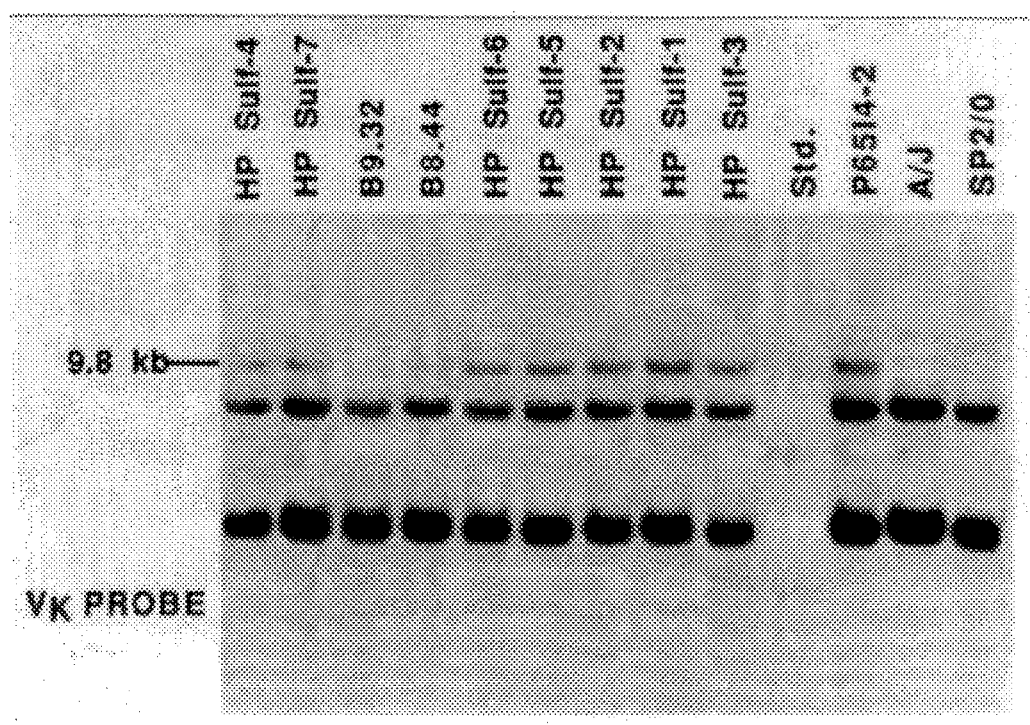
FIG. 1B also involves Southern blotting, using DNA digested with BamHI, and hybridized with a $V_K Id^{CR}$ probe.
Figure 2:
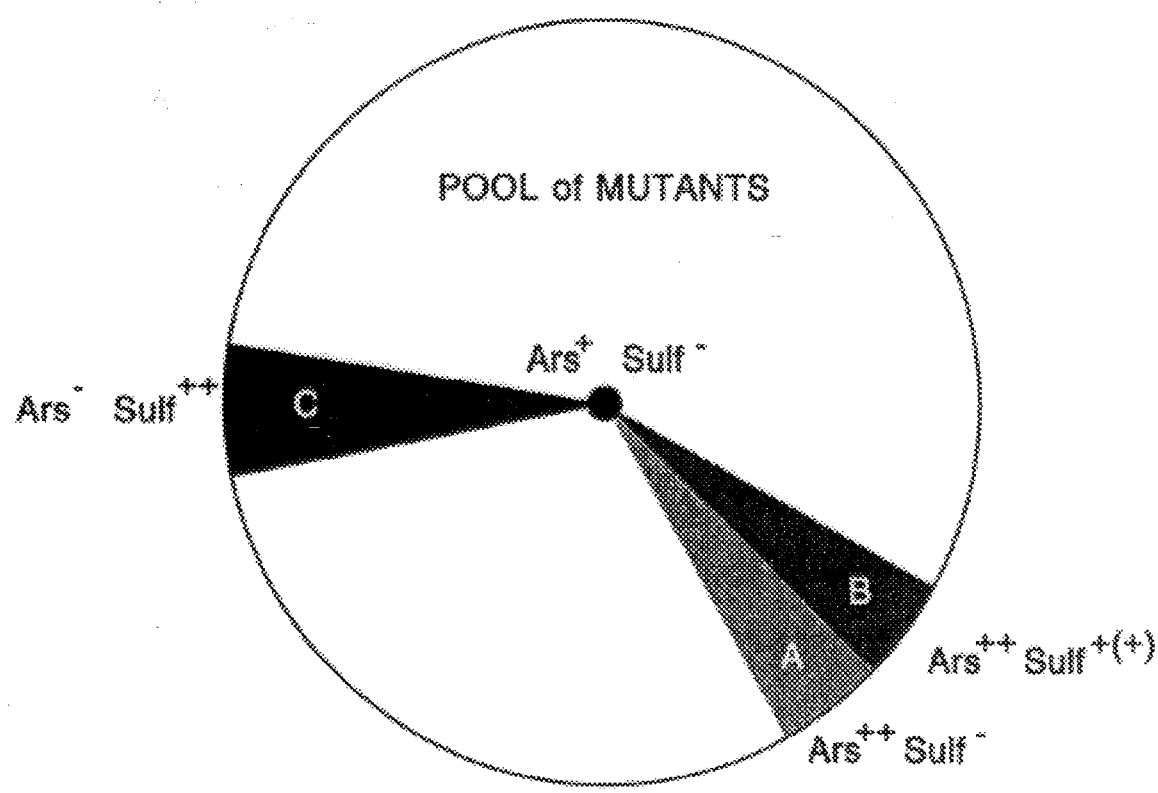
FIG. 2 sets forth a "piechart" summarizing the influence of mutation and selection on antigenic specificity. The full circle shows the pool of somatic mutants generated from a single, canonical precursor. Selection by Ars yields mutant B cells with enhanced affinity for Ars. This is segment "A" of the chart. Some of the B cells acquire Sulf specificity, i.e., "Segment B". Selection with Sulf during the period of mutational diversification results in B cells which have acquired Sulf specificity, but have lost it for Ars ("segment C").

Mice of strain A/J, when immunized with protein conjugates of p-azo phenylarsonate ("Ars"), frequently show, as part of their secondary immune response, antibodies which share the major idiotype "$Id^{CR}$". The $Id^{CR}$ idiotype is defined by rabbit antiserum which binds to the variable region of the antibody. A major subset of these antibodies is encoded by a single combination of variable genes. The antibodies coded for by this combination of genes are referred to as "canonical antibodies". The combination of variable genes has been reported in the literature—i.e., $V_H Id^{CR}$, Df116.1, $J_{H2}$, $V_K Id^{CR}$, $J_{K1}$ (see Siekvitz et al., Eur. J. Immunol. 13: 123 (1982); Wysocki et al., Proc. Natl. Acad. USA 83: 1847 (1986); Wysocki et al., J. Exp. Med. 166: 1 (1987)). Among the group of unmutated canonical antibodies, the variable regions have been observed to differ at codons 100 and 107, which are located at the junctional boundaries of the heavy chain variable gene segments. The near identity among unmutated canonical antibodies makes it possible to identify somatic mutations and to determine the influence of these on the antigenic specificity and affinity of the antibody.

The experiments which are set out in this and the following examples explain the invention in a series of steps. They show that among naturally occurring canonical mutant antibodies generated by immunization with Ars, there are individual antibodies which have lost capacity to bind Ars, but have acquired the ability to bind antigen "Sulf" (sulfanilic acid). It is then shown that it is possible to select subclones of mutant B cells producing these antibodies which are of changed specificity in that they bind Sulf. Of central importance is that these antibodies have lost their ability to bind Ars.

Studies were carried out to measure both serum antibody and idiotype concentration in mice which were immunized with Ars-KLH or Sulf-KLH. The immunization protocol involved 250 µg doses of the immunogen in complete Freund's adjuvant, administered interperitoneally. Animals (A/J mice) were bled after five weeks, and serum antibody and idiotype concentrations were determined, using a standard competitive assay (Woodland et al., Eur. J. Immunol. 8: 600 (1978)). Total antibody concentrations were determined in a direct binding assay, generally following Woodland et al., supra. In all tests, the limit of detection of the assay was 2 ug/ml.

The results of the study which follow in Table 1, showed that the levels of Anti-Sulf antiserum resulting from immunization with Ars-KLH alone are almost non-existent. Much more important, however, as a first step in the development of the invention, is the observation that the immunization with Sulf did not elicit antibodies of $Id^{CR}$ phenotype. The results in Table 1, which follow, show this. Thus, if any anti-Sulf antibodies of idiotype $Id^{CR}$ occur in later experiments, one can assume that these resulted from recruitment and mutational diversification of precursor $Id^{CR}$ stimulated by immunization with an alternative antigen (e.g. Ars). Experiments to determine if this could be done were carried out, and are described in the following examples.

Keyhole Limpet Hemocyanin complexes ("Sulf-KLH") in saline solution, 11, 13 and 15 days after the Ars-KLH immunizations. Eighteen days after the first Ars-KLH immunization, spleens were removed, and hybridoma fusions using Sp2/O-Ag-14 cells were carried out, following Gefter, M. L., Som. Cell Genet. 3: 231–236 (1977). The second animal received booster injections with a mixed conjugate of KLH and nine Sulf residues for each Ars residue.

The hybridomas which resulted were tested in a series of ways. One test was to determine if the antibodies being produced were canonical. A second test was carried out to determine whether the antibodies were of $Id^{CR}$ phenotype. This was important because it is known that Ars provokes generation of $Id^{CR}$ antibodies and the canonical subset thereof in A/J mice, and also that Sulf-KLH does not provoke generation of $Id^{CR}$ antibodies. See, e.g., Fish et al, J. Exp. Med. 170: 1191 (1989), and example 1, supra.

To determine expression of canonical antibodies, the hybridomas were tested in an mRNA assay to determine whether these expressed $V_K Id^{CR}$ and $V_H Id^{CR}$ gene segments. This assay permits identification of canonical candidates without regard to antigen specificity (Manser et al., Proc. Natl. Acad. Sci. USA 81: 2470 (1984)). This assay essentially uses the dot blot procedure of Manser et al., supra, which is incorporated by reference in its entirety.

The dot blot assay provides a preliminary test of which hybridomas express the required segments. Those which seemed to do so were then subjected to further testing in a Southern blot assay, following Siekevitz et al., supra and Wysocki et al., J. Exp. Med. 166: 1 (1987), both of which are incorporated by reference in their entirety. This assay permitted determination of any rearrangement of $V_H Id^{CR}$ and $V_K Id^{CR}$ segments. Essentially, the assay determines the combination of "V" and "J" regions—i.e. what "J" region is joined to the V region. In particular, one is assaying for $V_H Id^{CR} J_{H2}$ and $V_K Id^{CR} J_K$. When the Southern blotting was completed, six hybridomas were found which showed the appropriate band pattern, as well as a seventh one, with a differing band pattern. The six antibodies are potentially canonical.

All seven antibodies were analyzed further. The hybridomas which produce the monoclonal antibodies as well as the

TABLE 1

| | Serum antibody and idiotype concentrations in mice immunized with Ars-KLH and Sulf-KLH | | | |
|---|---|---|---|---|
| Immunogen* | Mouse | $Id^{CR}$ (µg/ml) | Anti-Ars (µg/ml) | Anti-Sulf (µg/ml) |
| Ars-KLH | 1 | 387 | 406 | 8 |
| | 2 | 257 | 360 | <2 |
| | 3 | 260 | 591 | 16 |
| | 4 | 294 | 301 | 21 |
| | 5 | 74 | 85 | 6 |
| Sulf-KLH | 1 | <2 | 6 | 2100 |
| | 2 | <2 | <2 | 2555 |
| | 3 | <2 | <2 | 488 |
| | 4 | <2 | <2 | 1075 |
| | 5 | <2 | <2 | 450 |
| | 6 | <2 | <2 | 338 |

Example 2

Two A/J mice were immunized intraperitoneally with 300 ug of the Ars protein coupled to Keyhole Limpet Hemocyanin ("Ars-KLH"), in complete Freund's adjuvant. One of the two animals received booster injections of sulfanilic acid— monoclonal themselves are referred to hereafter as "HP Sulf-1" through "HP Sulf-7". HP Sulf-1, 2 and 3 were all produced from fusions of B cells taken from the animal immunized with Sulf-KLH, while HP Sulf-4, 5, 6 and 7 were obtained from the animal immunized with the mixed conjugate.

The potentially canonical antibodies were then tested further, in immunoassays to determine (i) were they of idiotype $Id^{CR}$, and (ii) was their specificity to Ars or to Sulf? To determine these properties, the sensitive assays of Woodland et al., Eur. J. Immunol. 8: 600 (1987) were followed. Table 2 summarizes the results. All seven antibodies were of $Id^{CR}$ phenotype, did not bind Ars, but did bind Sulf in these sensitive assays. This was confirmed using a fluorescence quenching method according to Rothstein et al., Mol. Immunol. 20: 161 (1983). The fluorescence quenching assays confirmed that all seven antibodies bound Sulf-tyrosine, but not Ars-tyrosine, and six of these bound the Sulf derivative with an affinity greater than, or equal to, the affinity of known, canonical antibodies for Ars-tyrosine (Table 3). The identification of antibodies with $Id^{CR}$ idiotype which are specific for Sulf has important implications. Referring back to example 1, supra, one notes that no $Id^{CR}$ idiotype antibodies were generated following immunization with the Sulf immunogen. All $Id^{CR}$ antibodies were elicited by immunization with Ars.

The results secured herein, and summarized in Tables 2 and 3, strongly suggest that cells producing antibodies of $Id^{CR}$ idiotype, formerly specific to Ars, have mutated to produce sulf specific antibodies without a change in idiotype. Further, the results suggest that the antibody response (i.e., the Sulf specific antibodies) must derive from the prior Ars specific B cell subpopulation of $Id^{CR}$ producers, since Sulf specific antibodies elicited directly by immunization with Sulf are not of $Id^{CR}$ phenotype.

To determine the hapten specificity the sensitive assays of Woodland supra antibodies were followed, using complexes of either of Ars or Sulf and bovine serum albumin ("BSA"). Test wells were coated with conjugates of Ars or Sulf and BSA or unconjugated BSA alone. They were incubated with purified monoclonal antibodies (200 ng), from the hybridomas, washed, and then incubated with $^{125}I$ labelled rat monoclonal antibody directed against mouse kappa chains. Counts per minute ("cpm") of bound radioactivity were determined, and these data are presented in Table 2, which also follows. The data are averages of triplicate runs, after subtracting cpm bound to BSA coated wells.

TABLE 2

Hapten specificities of monoclonal antibodies*

| Hybridoma | CPM binding to: | |
|---|---|---|
| | Sulf-BSA | Ars-BSA |
| ±HPSulf-1 | 3,390 ± 169 | 11 ± 13 |
| ±HPSulf-2 | 3,907 ± 69 | 20 ± 29 |
| ±HPSulf-3 | 2,348 ± 39 | −6 ± 22 |
| HPSulf-4 | 3,818 ± 105 | 11 ± 4 |
| HPSulf-5 | 4,537 ± 84 | −14 ± 49 |
| HPSulf-6 | 3,809 ± 177 | 12 ± 31 |
| HPSulf-7 | 5,857 ± 130 | 58 ± 11 |

All of HP Sulf-1 through HP Sulf-7 have $Id^{CR}$ phenotype.

The assay utilized to generate Table 2 is an extremely sensitive one. What it shows is that the $Id^{CR}$ antibodies have no specificity to Ars whatsoever. In contrast, the specificity to Sulf is striking. This is decisive evidence that the $Id^{CR}$ antibodies bind Sulf but not Ars. Since $Id^{CR}$ antibodies cannot be directly elicited by Sulf, as shown by the data of Table 1, the results of this example indicate that the eliciting of Sulf binding $Id^{CR}$ antibodies was dependent upon prior immunization with Ars.

It must be pointed out that the hybridoma HP H/S, described in Table 3, infra is a canonical, Ars specific antibody producer. This antibody and the gene segments encoding it were used for comparison in the examples which follow.

TABLE 3

Affinities of monoclonal antibodies for Sulf-tyrosine and Ars-tyrosine*

| Hybridoma | $K_a$ for Ars-tyr (L/M) | $K_a$ for Sulf-tyr (L/M) |
|---|---|---|
| HP H/S± | $2.3 \times 10^6$ | $<5 \times 10^4$ |
| HPSulf-1± | $<5 \times 10^4$ | $2.8 \times 10^6$ |
| HPSulf-2± | $<5 \times 10^4$ | $1.3 \times 10^6$ |
| RPSulf-3± | $<5 \times 10^4$ | $1.3 \times 10^6$ |
| HPSulf-4 | $<5 \times 10^4$ | $5.6 \times 10^5$ |
| HPSulf-5 | $<5 \times 10^4$ | $1.9 \times 10^6$ |
| HPSulf-6 | $<5 \times 10^4$ | $1.3 \times 10^6$ |
| HPSulf-7 | $<5 \times 10^4$ | $3.8 \times 10^6$ |

Example 3

As was pointed out, supra within the canonical antibodies produced in response to Ars, two positions of variability are present at codons 100 and 107 at the boundaries of the heavy chain variable gene segments. As the data from examples 1 and 2 strongly suggested that antibodies of $Id^{CR}$ idiotype and Ars specificity had been recruited to Sulf specificity, it was of interest to study the actual nucleotide sequences of the gene segments coding for the variable regions of the antibodies.

Rearranged variable genes from the genomic DNA of the seven hybridomas were sequenced. Experimentally, the genes were amplified using a nested primer PCR methodology, followed by direct sequencing and without cloning, in accordance with Liu et al., Proc. Natl Acad. Sci. USA 89: 7610 (1992), the disclosure of which is incorporated by reference. The sequences are presented in Table 4, which follows.

Analysis of these sequences shows that of the seven antibodies, three were coded for entirely by canonical gene segments (HP Sulf-1, 2, and 3). This was determined by comparison to the known Ars specific canonical antibody, referred to by "Germline" in the Table. The four additional antibodies were nearly canonical. Two differed from canonical type only by insertion of a single codon in the D segment. Following Table 4 shows the differences between the seven antibodies. Table 5 is a "close-up" of the D segments of interest.

Of critical importance is the finding that the canonical hybridoma HP Sulf-1 contains residues at positions 100 and 107 in the D segment boundaries that are identical to those of the unmutated canonical antibody HP H/S. That is to say, the only differences between HP Sulf-1 and HP H/S are the somatic mutations in the heavy and light chain variable regions of the former (Table 4). Note that in Table 3, these antibodies have reciprocal specificities for Ars and Sulf. Ergo, the sequence data together with the affinity (binding) data prove that the somatic mutations alone are responsible for the different antigenic specificity (Sulf) of HP-Sulf-1.

Since somatic mutations are not induced unless a B cell is stimulated by antigen and since immunization with Sulf cannot directly stimulate unmutated canonical $Id^{CR}$ producing B cells, one must conclude that stimulation by Ars recruited the Id$^{CR}$ clones and induced their mutational diversification to include members that had acquired specificity for Sulf. Booster injections with Sulf then selected the mutant Sulf-binding B cell subclones for further expansion making possible their immortalization by the hybridoma formation process. Of special importance is the additional observation that the Sulf-binding mutants lack affinity for Ars altogether (Tables 2 and 3). This demonstrates that it is possible to recruit mutant B cells that have lost antigenic specificity for a stimulatory antigen (in this example, Ars) while acquiring a new antigenic specificity. Note that these antibodies are not of the "cross-reactive" type, extensively reported in the literature by Manser et al. supra, Fish et al supra, and Eisen, Immunology: An Introduction to Molecular and Cellular Principles of the Immune System (Harper & Raw, 2d edition, 1974) which bind two related antigens because of structural similarities between the two antigens.

4A.

| | | | | | | | | | | | | | | | | | | | | | | | |
|---|---|---|---|---|---|---|---|---|---|---|---|---|---|---|---|---|---|---|---|---|---|---|---|
| Germline: | GAG | CTT | CAG | TCT | GGA | GCT | GAG | CTG | GTG | AGG | GCT | GGG | TCC | TCA | GTG | AAG | ATG | TCC | TGC | | | | |
| HP Sulf-1 | :: | | | | | | | | | | | | | | | | | | | | | | |
| HP Sulf-2 | | | | | | -G- | | | | | | | | | | | | | | | | | |
| HP Sulf-3 | | -' | | | | -G- | -' | | | | | | | | | | | | | | | | |
| HP Sulf-4 | | | | | | | | | | | | | | | | | | | | | | | |
| HP Sulf-5 | | | | | | | | | | | | | | | | | | | | | | | |
| HP Sulf-6 | | | | | | | | | | | | | | | | | | | | | | | |
| HP Sulf-7 | | | | | | | | | | | | | | | | | | | | | | | |

| | | | | | | 10 | | | | | | | | | | 20 | | | | | | | |
|---|---|---|---|---|---|---|---|---|---|---|---|---|---|---|---|---|---|---|---|---|---|---|---|
| | | | | | | | | | | | | | | | | | | | | | | | |

| | | | | | | | | | | | | | | | | | | | | | | | |
|---|---|---|---|---|---|---|---|---|---|---|---|---|---|---|---|---|---|---|---|---|---|---|---|
| Germline | AAG | GCT | TCT | GGA | TAT | CCA | ACA | TTC | ACA | AGC | TAC | ATA | AGG | AAC | TCC | AAA | CAC | ACG | CCT | AAG | GGA | CAG | GGC |
| HP Sulf-1 | | | | | | | | | | | | | | | | | | | | | | | |
| HP Sulf-2 | | -G- | | | | -T- | | | | | | | -G- | | | | | | | | | | |
| HP Sulf-3 | | -G- | | | | | | | | -A- | | | -G- | | | | | | | | | | |
| HP Sulf-4 | | | | | | | | | | | | | | | | | | | | | | | |
| HP Sulf-5 | | | | | | | | | | | | | | | | | | | | | | | |
| HP Sulf-6 | | | | | | | | | -G- | | | | -G- | | | | | | | | | | |
| HP Sulf-7 | | | | | | | | | | | | | | | | -C- | | | | | | | |

| | | | | | | 30 | | | | | | | | | 40 | | | | | | | | |
|---|---|---|---|---|---|---|---|---|---|---|---|---|---|---|---|---|---|---|---|---|---|---|---|

| | | | | | | | | | | | | | | | | | | | | | | | |
|---|---|---|---|---|---|---|---|---|---|---|---|---|---|---|---|---|---|---|---|---|---|---|---|
| Germline | CTG | GAA | TGG | ATT | GGA | TAT | ATT | AAT | CCT | AGC | AAT | GGT | TAT | ACT | AAG | TAC | AAT | GAG | AAG | TTC | AAG | CAG | GGC |
| HP Sulf-1 | -C | | | | | | G- | | | | | -A- | | -TA | | | | | | | | | |
| HP Sulf-2 | | | | | | | | | | | | -A- | | -TA | -C | -C | | | | | | | |
| HP Sulf-3 | | | | | | | | | | | | -T- | | | -C | -C | | | | | | | |
| HP Sulf-4 | | | | | | | | | | | | -A- | | | -T | | | | | | -A | | |
| HP Sulf-5 | | | | | | | | | | -G- | | | | | -C | -C | | | | | | | |
| HP Sulf-6 | | | | | | | | | | | | | | | | | | | | | | | |
| HP Sulf-7 | | | | | | | | | | | | | | | | | | | | | | | |

| | 50 | | | | | | | | | | | | | | 60 | | | | | | | | |
|---|---|---|---|---|---|---|---|---|---|---|---|---|---|---|---|---|---|---|---|---|---|---|---|

| | | | | | | | | | | | | | | | | | | | | | | | |
|---|---|---|---|---|---|---|---|---|---|---|---|---|---|---|---|---|---|---|---|---|---|---|---|
| Germline | AAG | ACC | ACA | CTG | ACT | GTA | GAC | AAA | TCC | AGC | AGC | ACA | GCC | TAT | ATG | CAG | CTC | AGA | AGC | CTG | ACA | TCT | GAG |
| HP Sulf-1 | | | C- | | | | | | | | | | | | | | | | | | | | |
| HP Sulf-2 | | | | | | | | | | | | | -T- | | | | | | | | | | |
| HP Sulf-3 | | | | | | | | | | | | | | | | | -A | | | | | | |
| HP Sulf-4 | | | | | | | | | | | | | | | | | | | | | | | |
| HP Sulf-5 | | | | | | | | | | | | | | | | | | | | | | | |
| HP Sulf-6 | | | | | | | | | | | | | | | | | | | | | | | |
| HP Sulf-7 | | | | | | | | | | | | | | | | | | | | | | | |

| | | | 70 | | | | | | | | | | | | 80 | | | | | | | | |
|---|---|---|---|---|---|---|---|---|---|---|---|---|---|---|---|---|---|---|---|---|---|---|---|

| | | | | | | | | | | | | | | | | | | | | | | | |
|---|---|---|---|---|---|---|---|---|---|---|---|---|---|---|---|---|---|---|---|---|---|---|---|
| Germline | GAC | TCT | GCA | GTC | TAT | TTC | TGT | GCA | TCC | ACA | Ser | | | | | | | | | | | | |
| HP Sulf-1 | | | | | | | | | | | TC- | | | | | | | | | | | | |
| HP Sulf-2 | | | | | | | | | | | -C | | | | | | | | | | | | |
| HP Sulf-3 | | | | | | | | | -T | | -C | | | | | | | | | | | | |
| HP Sulf-4 | | | | | | | | | | | -C | | | | | | | | | | | | |
| HP Sulf-5 | | | | | | | | | | | -G | | | | | | | | | | | | |
| HP Sulf-6 | | | | | | | | | | | -C | | | | | | | | | | | | |
| HP Sulf-7 | | | | | | | | | -T | | -T | | | | | | | | | | | | |

| | 90 | | | | | | | | | | | 100 | | | | | | | | D | | | 107 |
|---|---|---|---|---|---|---|---|---|---|---|---|---|---|---|---|---|---|---|---|---|---|---|---|

| | | | | | | | | | |
|---|---|---|---|---|---|---|---|---|---|
| | | | | | | | | | |
| HP Sulf-1 | --- | CAT | TAC | TAT | GGT | AGC | TAC | --- | TCC | |
| HP Sulf-2 | TTT | CAT | --- | -C- | | -G-G | | | TGC | |
| HP Sulf-3 | TCT | CAT | --- | -C- | | -C-- | | | TGC | |
| HP Sulf-4 | ACC | | -T | | -A | AGC | TAC | | TAC | |
| HP Sulf-5 | TAT | | | | | | | | CTC | |
| HP Sulf-6 | TTT | | | -T- | | | | | AGC | |

| | | | | | | | | | | | | | | | |
|---|---|---|---|---|---|---|---|---|---|---|---|---|---|---|---|
| HP Sulf-7 | : | — | — | — | — | — | — | — | — | —T | — | —T | —T | —T | TGG |

| | | | | | | | | | | | | | | |
|---|---|---|---|---|---|---|---|---|---|---|---|---|---|---|
| | | | | 110 | | | | JH | | | | | 120 | |
| | | TTT | CAC | TAC | TCC | CCC | CAA | CCC | ACC | ACT | CTC | ACA | GTC | TCC | TCA | |
| Germline | : | | | | | | | | | | | | | | | |
| HP Sulf-1 | : | — | — | — | — | — | — | — | — | — | — | — | — | — | — | JH2 |
| HP Sulf-2 | : | — | — | — | — | — | — | — | — | — | — | : | — | — | — | JH2 |
| HP Sulf-3 | : | — | — | — | — | — | — | — | — | — | — | : | — | — | — | JH2 |
| HP Sulf-4 | : | — | — | — | — | — | — | — | — | — | — | : | — | — | — | JH2 |
| HP Sulf-5 | : | — | — | — | — | — | — | — | — | — | — | — | — | — | — | JH2 |
| HP Sulf-6 | : | —C | —T | GT— | — | — | AC— | —G | — | —G | G— | —C | — | — | — | JH2 |
| HP Sulf-7 | : | TAC | | | | | | | | | | | | | | JH1 |

FIG. 4B.

TABLE 5

| | | | D SEGMENT | | | | | | | | |
|---|---|---|---|---|---|---|---|---|---|---|---|
| | | | 100 His | | | | | | | | 107 Ser | |
| HP H/S Germline (IgG2b canonical): | TCN | CAT His | TAC | TAT | | GGT | GGT | AGC | TAC | TCC Ser | JH2 |
| HPSulf-1 (IgG2b, canonical): | —C | — | — | — | | — | — | — | — | — | JH2 |
| HPSulf-2 (IgG3, canonical): | —C | His — | — | C— | | — | — | — | — | Cys -G- | JH2 |
| HPSulf-3 (IgG1, canonical): | —C | His — | — | C— | | — | — | — | — | Cys -G- | JH2 |
| HPSulf-4 (IgG3, not canonical): | —G | ACC | —T | — | AGC | —A | —G | G-G | — | -A- | JH2 |
| HPSulf-5 (IgG1, not canonical): | —C | TTT T— | — | — | | — | — | — | -C- | GT- | JH2 |
| HPSulf-6 (IgG1, not canonical): | —T | TCT TT- | — | -T- | | — | — | — | — | AG- | JH2 |
| HPSulf-7 (IgG3, not canonical): | —T | | — | — | | — | — | —T | —T | -GG | JH1 |

Example 4

The differences in specificity between the Ars and Sulf specific antibodies could only have occurred by changes within the variable regions. To confirm this, the deduced amino acid sequences for the nucleotide sequences of the variable regions discussed in Example 3 were compared. Table 6 summarizes the somatic mutations that result in amino acid replacements in the antibody variable regions. Note that in HP Sulf-1 and in five of the remaining six antibodies, a common mutation at position 35 in the heavy chain variable region converts an asparagine residue to a serine residue. The seventh antibody has a similar change— i.e.—asparagine to threonine (of all the amino acid residues, threonine is most similar to serine). These conserved mutational changes are very unusual because no amino acid replacements have been observed at position $V_H35$ in any of the previously sequenced $Id^{CR}$ anti-Ars antibodies known in the art.

Analysis of the gene rearrangement patters and the sequence differences in the heavy chains (see Tables 4 and 6, respectively) —especially the D and J regions, shows that there are at least five different precursor regions, indicating that the seven hybridomas were derived from fusions involving B cells of five different lineages. One must conclude from this that the conserved mutation at $V_H35$ happened five times, and is therefore strongly selected. Of further interest is the fact that published X-ray structures of a canonical Ars-binding antibody (Strong et al., Biochem 30: 3739 (1991)) indicate that the asparagine residue contacts the bound Ars hapten. These observations strongly suggest that the somatic mutations at position $V_H35$ are responsible for the loss in specificity for Ars and the gain in specificity for Sulf.

The foregoing examples establish that the Sulf binding antibodies which were produced were products of mutant B cells that were derived from precursor B cells originally stimulated to proliferate and mutationally diversity their antibody genes by immunization with Ars, and the results suggest a method for generating antibodies to a desired or chosen antigen. The method involves a first step in which the immune system, in particular the B cells of a test animal are stimulated. The stimulation sets a cascade of events into motion. A mixed population of B cells results, including those which produce antibodies to the target antigen. Other forms of stimulation may also be used, for example, administering a component, such as an antibody or antibody component, which binds to antibody receptors on the surface of B cells. Binding to these receptors is sufficient to stimulate the B cells response, and can be accomplished via the use of immunoglobulins, portions of immunoglobulins, synthetic peptides, and so forth. Following the first step, the animal is immunized with an immunogen that includes the chosen antigen, one which differs from the first antigen. The immunogen, be it the first or second one, may be the antigen of choice, or may combine the antigen of choice and a carrier molecule to which the antigen is linked such as KLH or some other material, which renders the antigen more immunogenic. This approach is particularly desirable when the chosen antigen is poorly immunogenic, such as a hapten, a steroid, etc. The second, chosen immunogen stimulates a subpopulation of the B cell population discussed supra.

The immunogen of choice may be part of a composition containing the usual adjuvants associated with immunogen compositions. The composition optionally contains amounts of the first immunogen as well. Specifically, at least a part of the subpopulation of B cells which produces antibodies to the first immuongen acquires somatic mutations in the genes

TABLE 6

| | $V_KId^{CR}$ | | | $V_HId^{CR}$ | | | | | | | | | | |
|---|---|---|---|---|---|---|---|---|---|---|---|---|---|---|
| | 30 | 43 | 104 | 9 | 27 | 31 | 35 | 38 | 51 | 56 | 58 | 59 | 69 | 79 |
| Germline | S | T | L | A | Y | S | N | K | I | G | T | K | T | A |
| HPSulf-1: | – | – | V | – | – | – | S | – | V | – | – | N | P | V |
| HPSulf-2: | N | – | – | G | – | N | S | – | – | D | I | N | – | – |
| HPSulf-3: | N | – | – | G | – | – | S | – | – | D | I | N | – | – |
| HPSulf-4: | – | – | – | – | F | – | S | – | – | V | – | N | – | – |
| HPSulf-5: | Y | – | – | – | – | G | S | – | – | D | – | N | – | – |
| HPSulf-6: | – | S | – | – | – | – | S | – | – | – | – | – | – | – |
| HPSulf-7: | – | A | – | – | – | – | T | T | – | – | I | T | – | – | coding for variable regions of antibodies. These mutations are manifested in the expression products of the antibody genes, in antibodies which bind to the second immunogen but have lost specificity for the first one. In a particularly preferred, but by no means required embodiment, the second immunization leads to antibodies which are identical to the first antibody in every respect except for the mutational changes in this variable, binding region. These changes may be as little as a modification in a single codon, leading to a single amino acid change in the second antibody. More extensive changes are also possible.

The choice of experimental animal is left to the skilled artisan, it being understood that "animal" as used herein refers to any non-human animal which possesses an active immune system. Particularly preferred are rodents, such as mice, rats and rabbits. In a particularly preferred embodiment, the animal is a transgenic animal which contains a gene coding for a human immunoglobulin molecule, such as a transgenic mouse. Such transgenic animals, which are known to the art, produce human immunoglobulin and would generate antibodies of desired specificity in the same way the animals of the foregoing examples do.

In one embodiment of the invention, so-called autoreactive animals, such as mouse strains NZB×SWR(F1) and MRL lpr/lpr animals may be used. "Autoreactive" animals do not require treatment to undergo B cell hypermutation. Such animals need only be immunized with the immunogen of choice when they are in an autoreactive state. Determination of when the animal is in such a state is easily determined by one skilled in the art.

The antibodies produced in accordance with the invention may be polyclonal or monoclonal, the latter being especially preferred. Monoclonal antibodies may be prepared using any of the standard methodologies known to the art, such as by fusion with a permanently culturable cell, such as a myeloma cell, or by infection with an immortalizing DNA sequence, such as Epstein Barr Virus ("EBV"). Production of monoclonal antibodies presupposes the existence of an antibody producing clone; thus the process as previously described is carried out prior to any of the steps taken to generate monoclonals. The aim is to render the antibody producing B cell permanently culturable itself, any of the foregoing methods being sufficient to do so.

The antibodies can also be produced via transfection of the DNA which codes for the antibody into a recipient cell. The foregoing examples demonstrate how the DNA of interest can be identified and sequenced, and production of antibodies in host cells, including both prokaryotes and eukaryotes is already well known to the art. Thus, the DNA of interest may be cloned out of the antibody producing B cell via PCR, e.g., or a "synthetic" gene may be produced. In either case, the sequence is then transfected into the host cell, such as $E.$ $coli$. Variations on this methodology, as well as others which will be apparent to the skilled artisan are not elaborated upon herein.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Method for producing an antibody which specifically binds to a chosen antigen, comprising:
　(i) immunizing an animal selected from the group consisting of an A/J mouse and a transgenic mouse possessing and ARS specific antibody gene segments, with a first immunogen which is not said chosen antigen to stimulate a B cell response thereto, said B cell response comprising:
　　(a) production of antibodies specific to said first immunogen;
　　(b) somatic hypermutation in the antibody variable gene repertoire of said B cell, and
　(ii) immunizing said non-human animal with a second immunogen less than 15 days after performing said immunization of step (i), wherein said second immunogen comprises said chosen antigen and is not said first immunogen, to stimulate proliferation of a subpopulation of said B cells which have undergone somatic hypermutation to produce antibodies specific to said chosen antigen wherein said first immunogen is a protein conjugate of p-azo phenylarsonate (ARS) and said second immunogen is a protein conjugate of sulfanilic acid (SULF).

2. The method of claim 1, further comprising isolating B cells of said subpopulation which produce antibodies specific to said chosen antigen and treating said B cells to immortalize said B cells.

3. The method of claim 2, comprising fusing said B cells with a myeloma cell line.

4. The method of claim 1, further comprising:
　(iii) isolating a nucleic acid which codes for an antibody specific to said chosen antigen from said B cells, said antibody having essentially no cross-reactivity with said first immunogen,
　(iv) transfecting a host cell with said nucleic acid molecule, and
　(v) culturing said host cell to produce said antibodies.

5. The method of claim 4, comprising culturing said host cell in a recipient non-human animal.

* * * * *